US011464544B2

(12) United States Patent
Eugene

(10) Patent No.: US 11,464,544 B2
(45) Date of Patent: Oct. 11, 2022

(54) AUTOMATIC FOOT CLEANER AND CALLUS REMOVER

(71) Applicant: Fritz Eugene, Brooklyn, NY (US)

(72) Inventor: Fritz Eugene, Brooklyn, NY (US)

( * ) Notice: Subject to any disclaimer, the term of this patent is extended or adjusted under 35 U.S.C. 154(b) by 475 days.

(21) Appl. No.: 16/739,380

(22) Filed: Jan. 10, 2020

(65) Prior Publication Data

US 2020/0222083 A1 Jul. 16, 2020

Related U.S. Application Data

(60) Provisional application No. 62/790,990, filed on Jan. 10, 2019.

(51) Int. Cl.
*A61B 17/54* (2006.01)
*A61H 35/00* (2006.01)
*A61H 15/00* (2006.01)
*A61H 11/00* (2006.01)
*A47K 7/02* (2006.01)
*A61B 17/32* (2006.01)

(52) U.S. Cl.
CPC .............. *A61B 17/54* (2013.01); *A47K 7/026* (2013.01); *A61H 11/00* (2013.01); *A61H 15/0078* (2013.01); *A61H 35/006* (2013.01); *A61B 2017/320004* (2013.01); *A61H 2201/10* (2013.01)

(58) Field of Classification Search
CPC ...... A61B 17/54; A47K 7/026; A61H 35/006; A61H 11/00; A61H 15/0078
USPC ............................................ 15/104.92; 4/622
See application file for complete search history.

(56) References Cited

FOREIGN PATENT DOCUMENTS

EP 1419758 A1 * 5/2004 ......... A61H 15/0078

* cited by examiner

*Primary Examiner* — Tuan N Nguyen
(74) *Attorney, Agent, or Firm* — MG Miller Intellectual Property Law LLC

(57) ABSTRACT

An automatic foot cleaner and callus remover is provided. Through the use of multiple flexible cleaning bands configured to scrub the heel and sole of a user's foot, as well as a toe cleaning mechanism, the automatic foot cleaner and callus remover is capable of cleaning the user's foot and removing any calluses on the user's foot. Optionally, the automatic foot cleaner and callus remover is filled with a liquid such as infused water to assist with the cleaning process.

9 Claims, 6 Drawing Sheets

AUTOMATIC FOOT CLEANER AND CALLUS REMOVER

CLAIM OF PRIORITY

This application claims priority to U.S. Provisional Patent Application No. 62/790,990, filed on Jan. 10, 2019, entitled "AUTOMATED HANDS FREE CALLUS REMOVER", the contents of which are hereby incorporated by reference, in their entirety.

NOTICE OF COPYRIGHTS AND TRADE DRESS

A portion of the disclosure of this patent document contains material which is subject to copyright or trade dress protection. This patent document may show and/or describe matter that is or may become trade dress of the owner. The copyright and trade dress owner has no objection to the facsimile reproduction by anyone of the patent disclosure, as it appears in the Patent and Trademark Office patent files or records, but otherwise reserves all copyright and trade dress rights whatsoever.

FIELD OF THE EMBODIMENTS

The present disclosure relates generally to an automatic foot cleaner and callus remover. More particularly, the present disclosure relates to an automatic foot cleaner and callus remover that enables a user to place their foot into said automatic foot cleaner and callus remover while the machine operates to have excess skin cells and other undesirable materials from the user's foot.

BACKGROUND

Despite the wide availability of places to receive a pedicure and other foot cleaning services, many people do not frequent such establishments, if they even go at all. When one patrons such a business, the complaints are relatively universal: the patron often feels like they are being gossiped about, and many feel self-conscious about the condition of their feet. Others feel that having another scrub their feet subjugates the scrubber, making the patron uncomfortable and preventing them from enjoying what is supposed to be a relaxing experience.

Further, pedicures and similar services can be very expensive, and can be time-consuming and difficult to schedule. Moreover, many people who want pedicures but for one reason or another, such as being elderly or disabled, cannot get these procedures or simply will not leave the house to get one.

Lastly, self-care is very popular today and many people are looking for things they can do in the comfort of their own home that will contribute to their well-being. Accordingly, there is a need for a hands-free device that is capable of cleaning a user's foot and removing calluses, that can be easily operated within the comfort of one's home and without requiring undue effort on the part of the user.

It is an object of the present invention to provide a means for a person to clean their feet and remove any callouses without exerting undue effort and within the comfort of their own home.

The present invention and its embodiments meets and exceeds this objective.

The present disclosure addresses at least one of the foregoing disadvantages. However, it is contemplated that the present disclosure may prove useful in addressing other problems and deficiencies in a number of technical areas. Therefore, the claims should not necessarily be construed as limited to addressing any of the particular problems or deficiencies discussed hereinabove. To the accomplishment of the above, this disclosure may be embodied in the form illustrated in the accompanying drawings. Attention is called to the fact, however, that the drawings are illustrative only. Variations are contemplated as being part of the disclosure.

SUMMARY

An aspect of an example embodiment in the present disclosure is to provide for an automatic foot cleaner and callus remover. Preferably, the cleaner will have a housing having a front end, a rear end, a left side and a right side both extending between the front end and the rear end, a bottom extending between the front end, the rear end, the left side and the right side, a top extending between the front end, the rear end, the left side and the right side, and an outer shell bounded by the front end, the rear end, the left side, the right side, the bottom, and the top. The top is shaped and sized to accommodate the insertion of a human foot into the housing.

The cleaner also includes a plurality of interior walls contained within the housing, where the plurality of interior walls form a fluid-impermeable tank, the tank having a drain reservoir and a drain having an open position and a closed position, the drain comprising a drain hole and a removably attached drain stopper. The tank is also shaped such that a fluid disposed in the tank will flow into the drain reservoir, where the drain is located such that gravity will direct fluids outside of the housing when the drain is in the open position.

The cleaner also includes a cavity, defined by the plurality of interior walls and the outer shell and a heel cleaning mechanism proximate to the rear end. The heel cleaning mechanism has a heel resting member disposed on the bottom, within the tank, a first motor located within the cavity, a first plurality of rollers, a first portion of which is located within the cavity, a second portion of which is located within the tank, and a first cleaning band. Here, the first cleaning band provides for the mechanical communication between the first motor and the first plurality of rollers, the first cleaning band is flexible, and is equipped with at least one abrasive material. The first motor is configured to actuate the first cleaning band.

Further, the automatic foot cleaner and callus remover includes a sole cleaning mechanism, which is made up of a second motor located within the cavity, a second plurality of rollers located within the tank, and a second cleaning band. Similarly to the first cleaning band, the second cleaning band provides for the mechanical communication between the second motor and the second plurality of rollers, the second cleaning band is flexible, is equipped with the at least one abrasive material, and extends from the left side to the right side. The second motor is configured to actuate the second cleaning band.

The automatic foot cleaner and callus remover in accordance with the present disclosure also features a toe cleaning mechanism which is proximate to the front end. The toe cleaning mechanism consists of a third motor located within the cavity, and a cleaning member that extends from the third motor into the tank. Preferably, the cleaning member is equipped with a plurality of bristles, and the third motor is configured to rotatably actuate the cleaning member. The automatic foot cleaner and callus remover also has a power source which is in electronic communication with the first motor, the second motor, and the third motor; and a processor and a memory, both in electronic communication with each other and the power source, the memory containing computer-readable instructions for the selective actuation of the first motor, the second motor, and the third motor.

In some embodiments, the automatic foot cleaner and callus remover in accordance with the present disclosure also includes a guidance insert which is shaped to rest on the top, wherein the guidance insert is sized and shaped to accommodate the insertion of a human foot into the housing. In other embodiments, the automatic foot cleaner and callus remover in accordance with the present disclosure also includes an essence oil infuser, configured to infuse essence oil(s) into any fluid placed in the tank.

In various embodiments, the first cleaning band and/or the second cleaning band are imbued with one or more abrasive materials. These materials are selected from the group consisting of sand, coral, quartz, glass, zirconia, cubic zirconia, turquoise, amethyst, black obsidian, emeralds, diamonds, and rubies. Depending on the desired configuration, the automatic foot cleaner and callus remover in accordance with the present disclosure can be configured to actuate the first cleaning band and/or the second cleaning band in a continuous motion or in a back-and-forth motion.

In other embodiments, the automatic foot cleaner and callus remover in accordance with the present disclosure features a fourth motor within the cavity that is connected to the second cleaning band. This provides for additional force to help the second cleaning band scrub with greater intensity. This fourth motor is in electronic communication with the power source and the processor and the memory.

Implementations may include one or a combination of any two or more of the aforementioned features.

These and other aspects, features, implementations, and advantages can be expressed as methods, apparatuses, systems, components, program products, business methods, and means or steps for performing functions, or some combination thereof.

Other features, aspects, implementations, and advantages will become apparent from the descriptions, the drawings, and the claims.

While these units may be suitable for the particular purpose employed, or for general use, they would not be as suitable for the purposes of the present disclosure as disclosed hereafter.

In the present disclosure, where a document, act, or item of knowledge is referred to or discussed, this reference or discussion is not an admission that the document, act, item of knowledge, or any combination thereof that was known at the priority date, publicly available, known to the public, part of common general knowledge or otherwise constitutes prior art under the applicable statutory provisions; or is known to be relevant to an attempt to solve any problem with which the present disclosure is concerned.

While certain aspects of conventional technologies have been discussed to facilitate the present disclosure, no technical aspects are disclaimed. It is contemplated that the claims may encompass one or more of the conventional technical aspects discussed herein.

BRIEF DESCRIPTION OF THE PREFERRED EMBODIMENTS

In the drawings, like elements are depicted by like reference numerals. The drawings are briefly described as follows.

The present disclosure now will be described more fully hereinafter with reference to the accompanying drawings, which show various example embodiments. However, the present disclosure may be embodied in many different forms and should not be construed as limited to the example embodiments set forth herein. Rather, these example embodiments are provided so that the present disclosure is thorough, complete, and fully conveys the scope of the present disclosure to those skilled in the art. In fact, it will be apparent to those skilled in the art that various modifications and variations can be made in the present invention without departing from the scope or spirit of the invention.

DETAILED DESCRIPTION OF THE PREFERRED EMBODIMENTS

Figure 1:
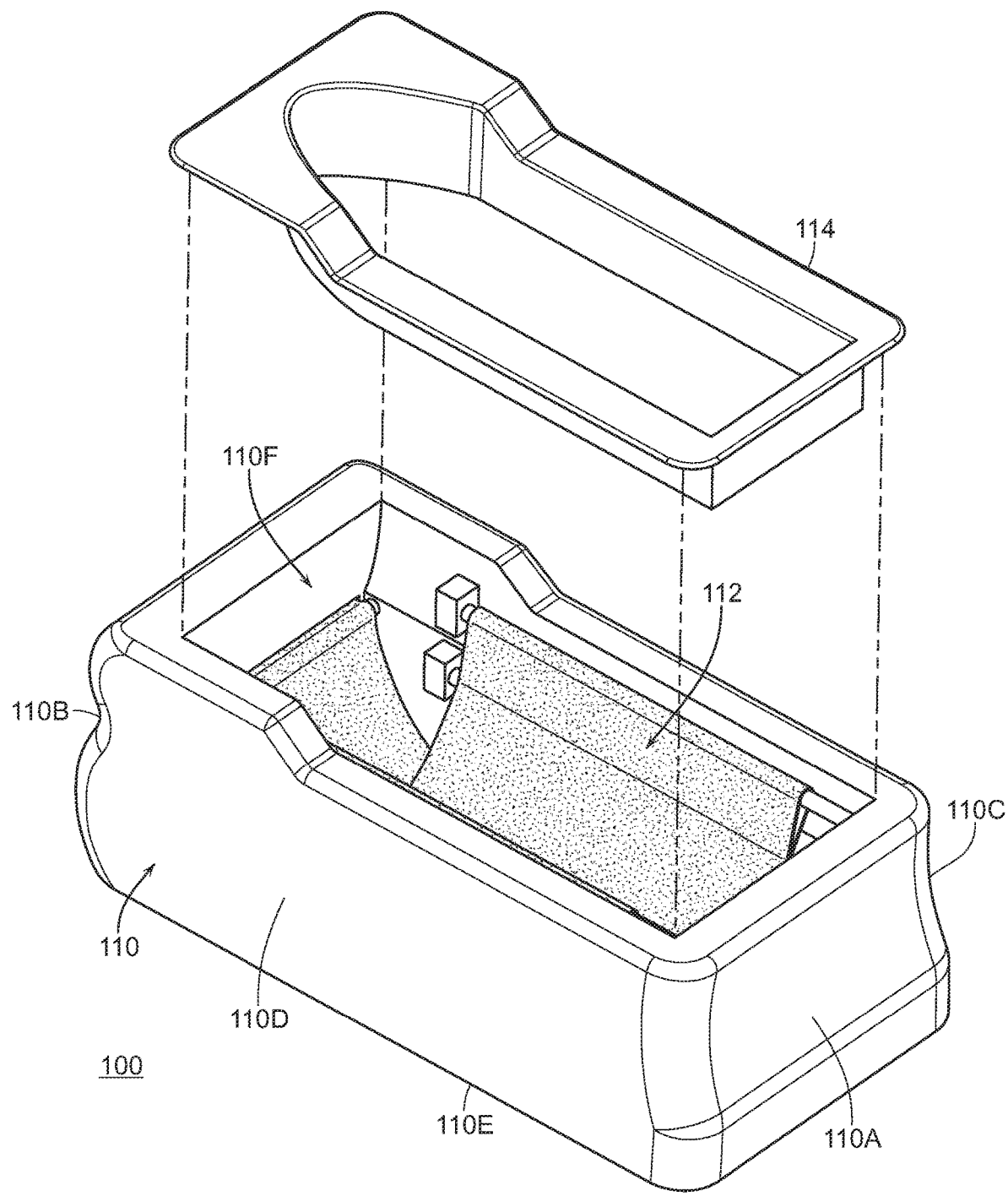
FIG. 1 is a perspective of an embodiment of the automatic foot cleaner and callus remover in accordance with the present invention showing how a guidance insert in accordance with the present disclosure interfaces with the automatic foot cleaner and callus remover.

FIG. 1 illustrates an embodiment of an automatic foot cleaner and callus remover 100 in accordance with the present disclosure. The automatic foot cleaner and callus remover 100 has a housing 110 has a front end 110A, a rear end 110B, a left side 110C, a right side 110D, a bottom 110E and a top 110F. The left side 100C and the right side 100D extend between the front end 110A and the rear end 110B. The bottom 110E and the top 110F span across the front end 110A, the rear end 110B, the left side 110C, and the right side 110D. The top 110F is equipped with a receiving port 112 which is sized and shaped to accommodate the insertion of a human foot into the automatic foot cleaner and callus remover 100.

FIG. 1 also shows a guidance insert 114 which is sized to rest on the top 110F. Further, the guidance insert 114 is also sized and shaped to further accommodate the insertion of a human foot into the receiving port 112. In some embodiments, the guidance insert 114 is shaped to indicate to the user how to place the user's foot within the automatic foot cleaner and callus remover 100. For example, as shown here, the guidance insert 114 will have a rounded portion and a flared portion, where the rounded portion indicates that the user should insert their heel proximate to the rounded portion. In various embodiments, the guidance insert 114 is removably attached to the top 110F. This removable attachment can be provided through a limited friction fit, hook-and-loop fasteners, magnets, a mild adhesive, and the like.

Figure 2:
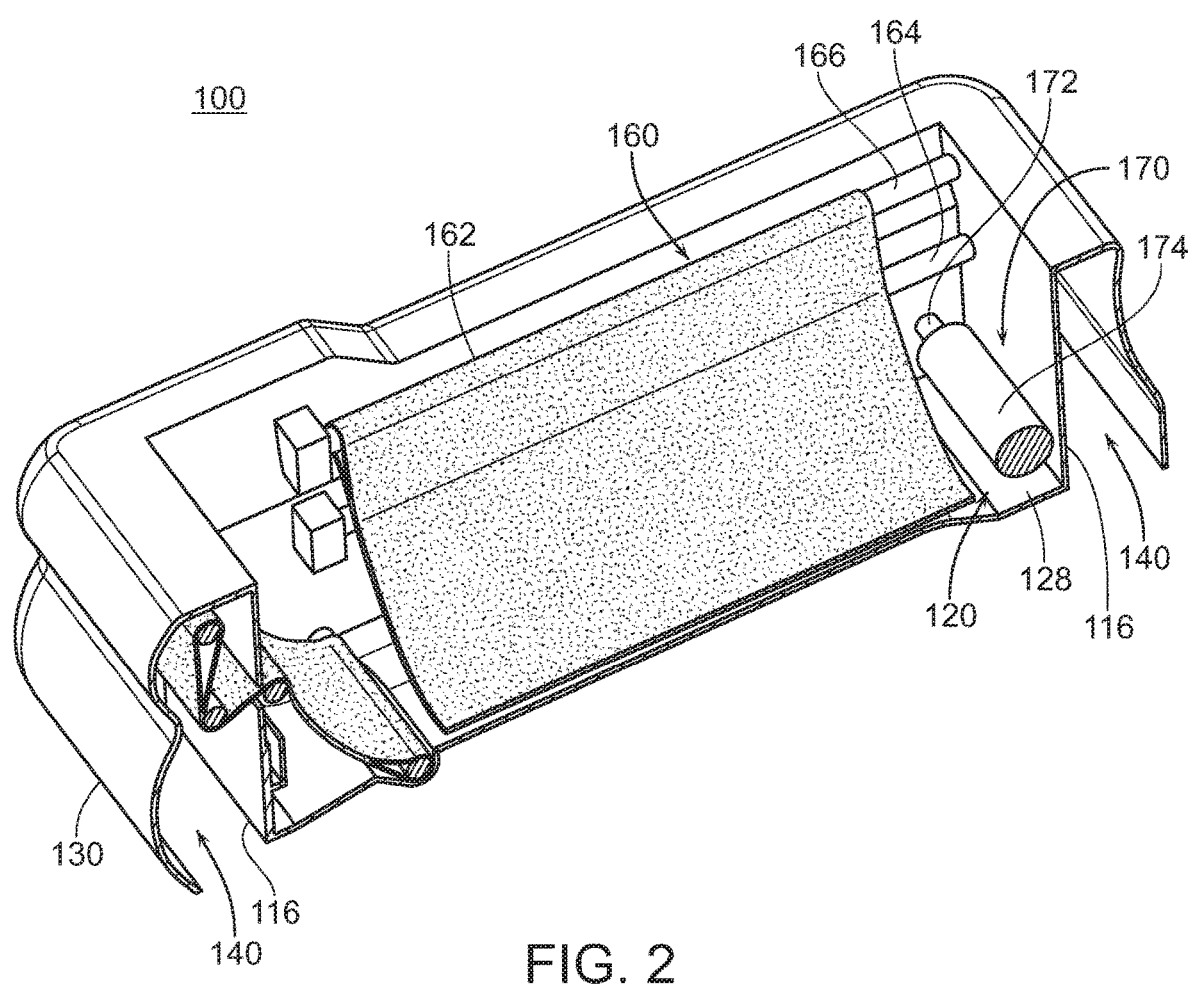
FIG. 2 is a perspective cross-sectional view of an embodiment of the automatic foot cleaner and callus remover in accordance with the present disclosure.

Referring to FIG. 2, a perspective view of a cross-section of an embodiment of the automatic foot cleaner and callus remover 100 is shown. Here, a sole cleaning mechanism 160 is shown. The sole cleaning mechanism 160 is equipped with a second cleaning band 162, a second motor 166, and a plurality of second non-motorized rollers 164. In some embodiments, the second motor 166 is a motorized roller with a high-friction material disposed thereon. This friction is used to generate grip with the second cleaning band 162, to provide for the actuation of the second cleaning band 162. The second cleaning band 162 is also in mechanical communication with a plurality of second non-motorized rollers 164, which is used to assist the second cleaning band 162 in achieving maximum contact with a human user's foot inserted in the automatic foot cleaner and callus remover 100.

Here, the automatic foot cleaner and callus remover 100 is also shown with a toe cleaning mechanism 170. The toe cleaning mechanism 170 is equipped with a third motor 172 which is attached to a cleaning member 174. In some embodiments, the third motor 172 is permanently attached to the cleaning member 174, while in other embodiments the third motor 172 is removably attached to the cleaning member 174. In various embodiments, the cleaning member 174 is equipped with a means for generating greater contact with the user's toes, such as bristles. The flexibility of these bristles can vary based on user preference. In a preferred embodiment, multiple cleaning members 174 are included with the automatic foot cleaner and callus remover 100 to allow a user to substitute one cleaning member 174 for another cleaning member 174, to meet their preference of bristle flexibility.

As can be seen here, the automatic foot cleaner and callus remover 100 has an outer shell 130 which is the outer bound of housing 110 (See FIG. 1). The automatic foot cleaner and callus remover 100 also is equipped with a plurality of interior walls 116 which bound a tank 120. The tank 120 is fluid-impermeable and contains a drain reservoir 128. The tank 120 has a bottom with a raised portion that extends downwardly towards the drain reservoir 128, which is configured to collect fluids placed in the tank. The automatic foot cleaner and callus remover 100 also includes a cavity 140, which is sized to house a power source used to control the second motor 166 and other electronic components, discussed below. The cavity 140 is also sized to house a computer configured to control the automatic foot cleaner and callus remover 100, also discussed below.

Figure 3:
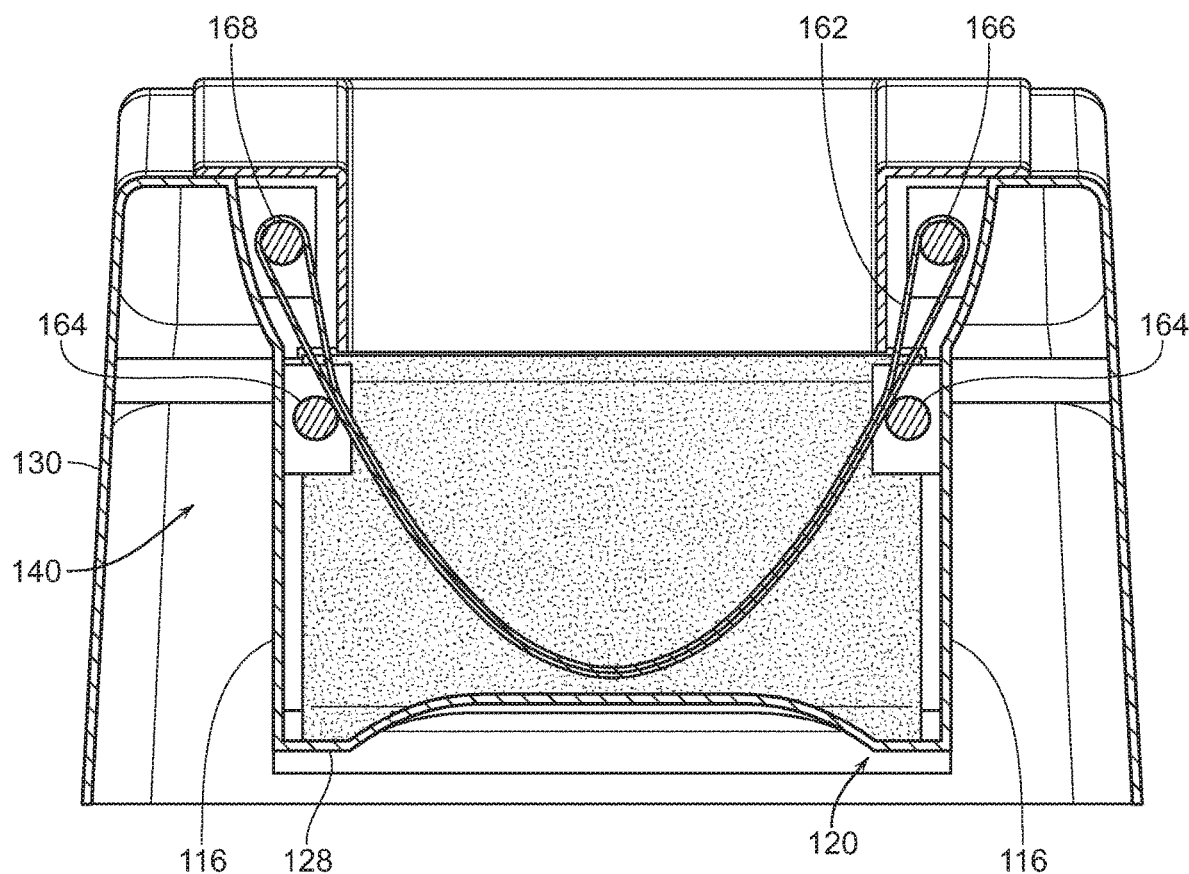
FIG. 3 is a front cross-sectional view of an embodiment of the automatic foot cleaner and callus remover in accordance with the present disclosure.

FIG. 3 shows a front view of a cross-section of an embodiment of the automatic foot cleaner and callus remover 100. Similarly to FIG. 2, the outer shell 130, the plurality of interior walls 116, and the cavity 140 which is formed by the outer shell 130 and the plurality of interior walls 116 are shown. Further, the slope of the bottom of the tank 120 which extends into the drain reservoir 128 is also shown here.

Of note in this view, is the configuration of the second cleaning band 162, the plurality of second non-motorized rollers 164, the second motor 166, and an optional fourth motor 168. Here, the second cleaning band 162 is releasably attached to the second motor 166, which is in a limited friction fit with the second cleaning band 162. In some embodiments the fourth motor 168 is replaced with an additional second non-motorized roller 164. In other embodiments, the fourth motor 168 is equipped, to provide greater force when actuating the second cleaning band 162. When fluid is placed within the tank 120, it is important that the second motor 166 and the fourth motor 168, if equipped, are not submerged in the fluid. In various embodiments, it is acceptable if any or all of the second non-motorized rollers 164 are submerged or partially submerged in the fluid.

In some embodiments, the second motor 166 and/or the fourth motor 168 are configured to actuate the second cleaning band 162 in a back-and-forth motion, while in other embodiments, the second motor 166 and/or the fourth motor 168 are configured to actuate the second cleaning band 162 in a continuous motion. Embodiments exists where one of the second motor 166 and the fourth motor 168 is configured for continuous actuation, while the other is configured for back-and-forth actuation. In these embodiments with a dual-configuration, it is important that both the second motor 166 and the fourth motor 168 do not simultaneously operate. Note that the second cleaning band 162 is flexible to accommodate the natural curves of the human foot. In some embodiments, the fourth motor 168 is a motorized roller with a high-friction material disposed thereon to assist with the integrity of the interface between the fourth motor 168 and the second cleaning band 162.

Figure 4:
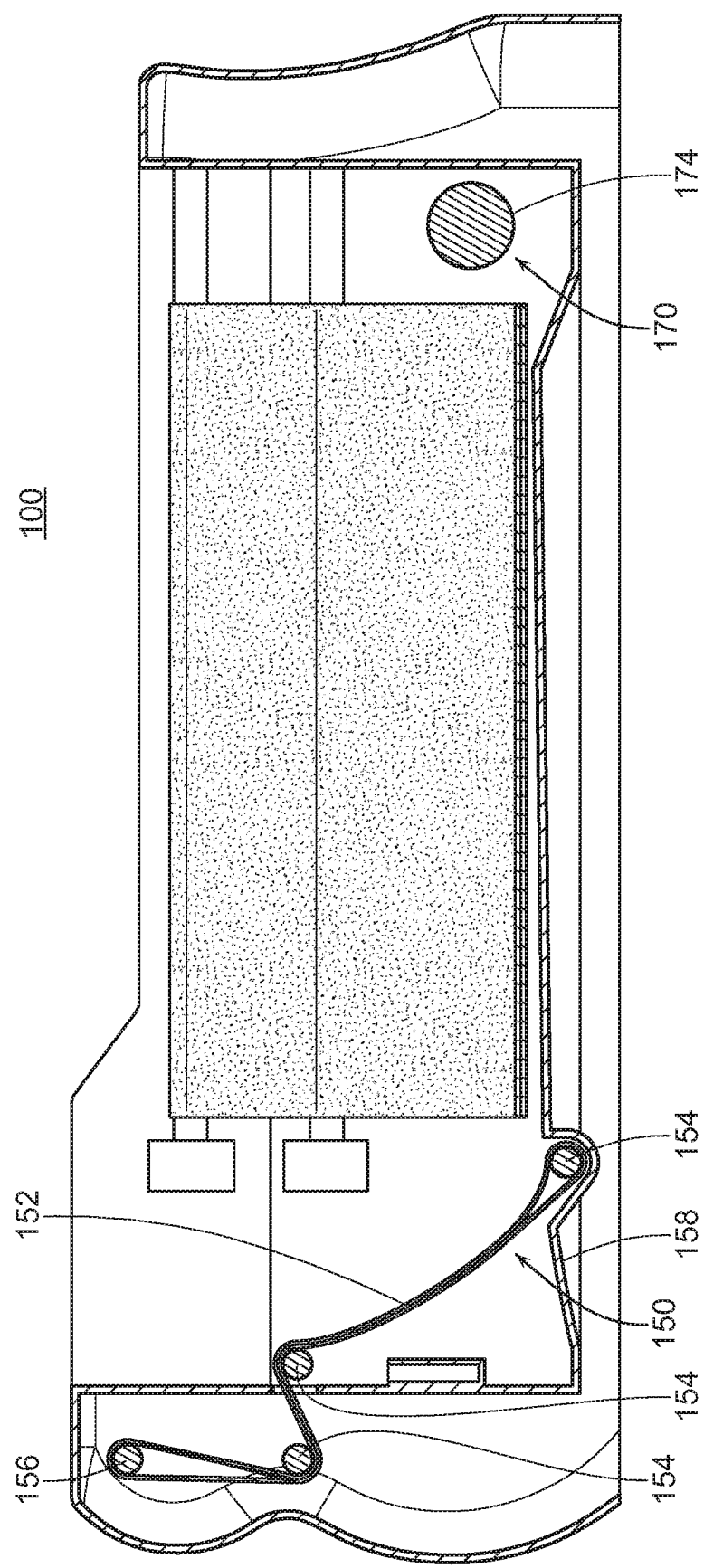
FIG. 4 is a right side cross-sectional view of an embodiment of the automatic foot cleaner and callus remover in accordance with the present disclosure.

Referring to FIG. 4, a side view of a cross-section of the automatic foot cleaner and callus remover 100 is provided. Here, the automatic foot cleaner and callus remover 100 is shown again with the toe cleaning mechanism 170 having the cleaning member 174 also shown. Of particular note is a heel cleaning mechanism 150 that is featured here. The heel cleaning mechanism 150 includes a heel resting member 158, which is to accommodate the placement of a user's heel when inserted into the automatic foot cleaner and callus remover 100.

The heel cleaning mechanism 150 also includes a plurality of first non-motorized rollers 154, which are in mechanical communication of a first cleaning band 152, which is also in mechanical communication with a first motor 156. The first motor 156 is located within the cavity 140 (See FIG. 3) so that when fluid is placed in the tank 120 (See FIG. 3) the first motor 156 will not come into contact with the fluid. It is permissible for any of the plurality of first non-motorized rollers 154 to be exposed to a fluid, provided that the first motor 156 will not simultaneously be exposed. The plurality of first non-motorized rollers 154 are in a configuration such that the first cleaning band will have a curvature corresponding to a human heel. Similarly to the second motor 166 (See FIG. 3) and the optional fourth motor 168 (See FIG. 3), embodiments exist where the first motor 156 is configured to continuously actuate the first cleaning band 152, and other embodiments exist where the first motor 156 is configured to actuate the first cleaning band 152 in a back-and-forth motion. Other embodiments exist where it is possible for a user to flip back and forth between these two types of actuation, through the use of an attached computer which is in electronic communication with the first motor 156. In some embodiments, the first motor 156 is a motorized roller with a high-friction material disposed thereon to assist with the integrity of the interface between the first motor 156 and the first cleaning band 152.

Figure 5:
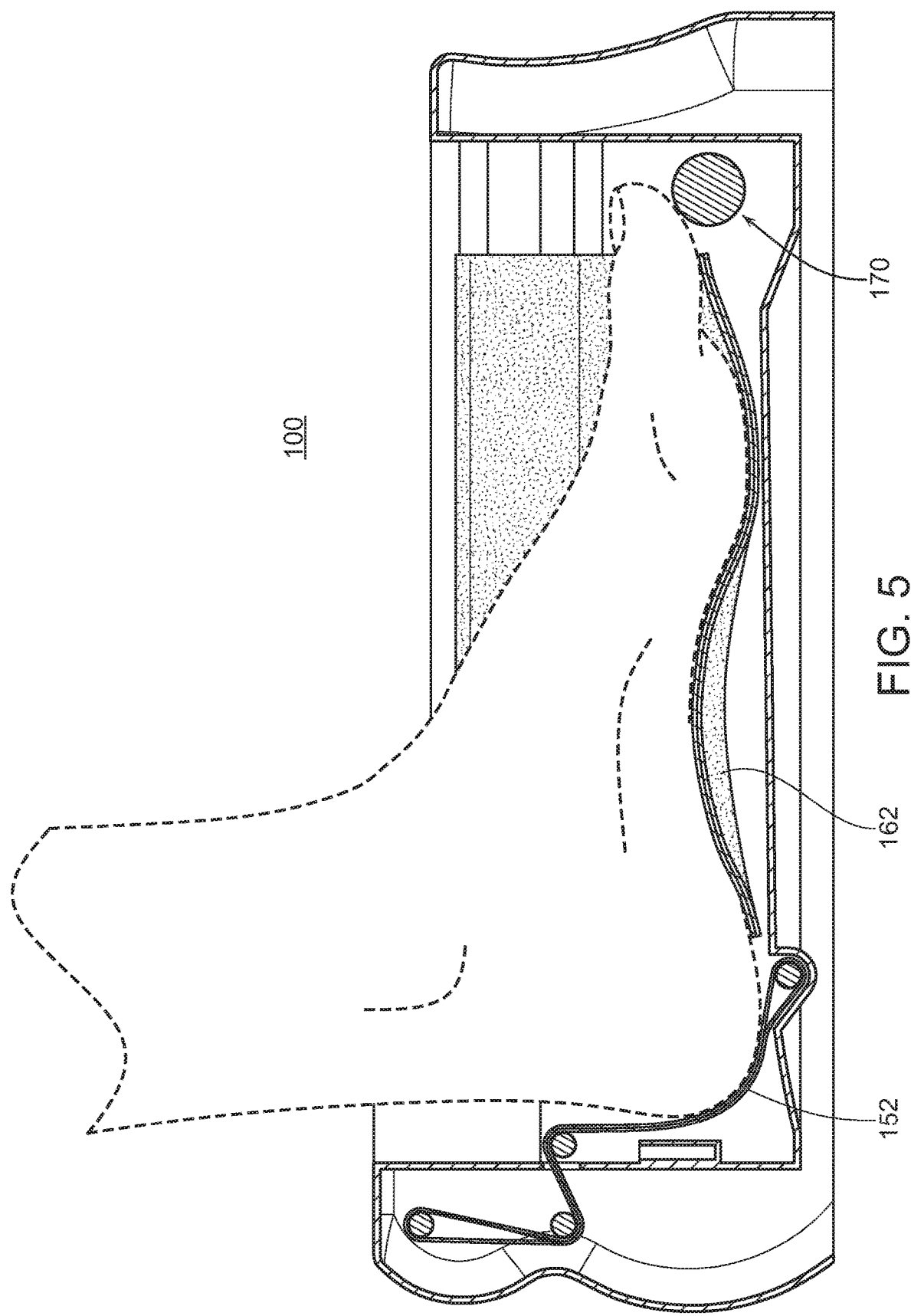
FIG. 5 is a right side cross-sectional view of an embodiment of the automatic foot cleaner and callus remover in accordance with the present disclosure, showing how a human foot would interface with said device.

In FIG. 5 a side view of a cross-section of the automatic foot cleaner and callus remover 100, showing an inserted human foot, is shown. Of note here is the conformity of the first cleaning band 152 and the second cleaning band 162 with the curves of the user's foot. Maximizing contact between the first cleaning band 152 and the user's foot, as well as the second cleaning band 162 and the user's foot is important so that no portion of the user's foot goes uncleaned. Further, FIG. 5 shows how the user's foot will interface with the toe cleaning mechanism 170. When one or more bristles are included with the toe cleaning mechanism 170, the bristles will be configured to clean spaces between the user's toes, as well as the user's toes themselves.

Figure 6:
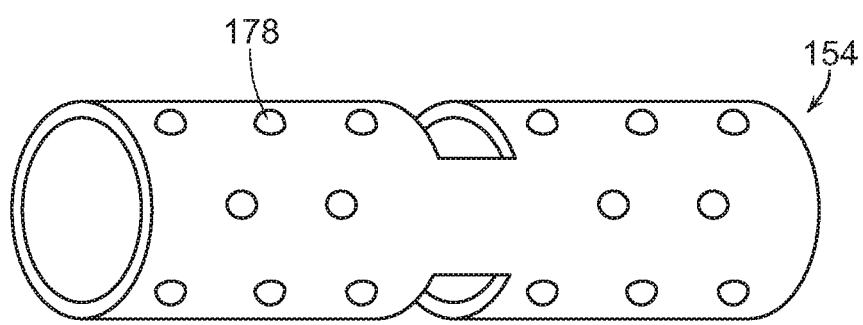
FIG. 6 is a perspective view of an embodiment of a roller in accordance with the present disclosure.

Referring to FIG. 6, an embodiment of one of the plurality of first non-motorized rollers 154 is shown. Note that while FIG. 6 makes references to the first non-motorized roller 154, this construction can also be used for the first motor 156, the second motor 166, the third motor 172, the fourth motor 168, and/or any or all of the plurality of second non-motorized rollers 164. In a highly preferred embodiment, all of the plurality of first non-motorized rollers 154, the first motor 156, the second motor 166, the third motor 172, the fourth motor 168, and/or any or all of the plurality of second non-motorized rollers 164 are all interchangeable, with the exception being that the first motor 156, the second motor 166, the third motor 172, and the fourth motor 168 are all configured to be actuated by the computer in accordance with the present disclosure.

Here, the embodiment shown is equipped with a plurality of high-friction contact points 178. These high-friction contact points 178 are constructed out of a material that will generate sufficient friction between said high-friction contact points 178 and any interfaced cleaning band. In other embodiments, any interfaced cleaning band may be attached to any of the plurality of first non-motorized rollers 154, the first motor 156, the second motor 166, the third motor 172, the fourth motor 168, and/or any or all of the plurality of second non-motorized rollers 164, through other, known means of removable attachment. These means include hook-and-loop fasteners, magnets, mild adhesives, and the like.

Figure 7:
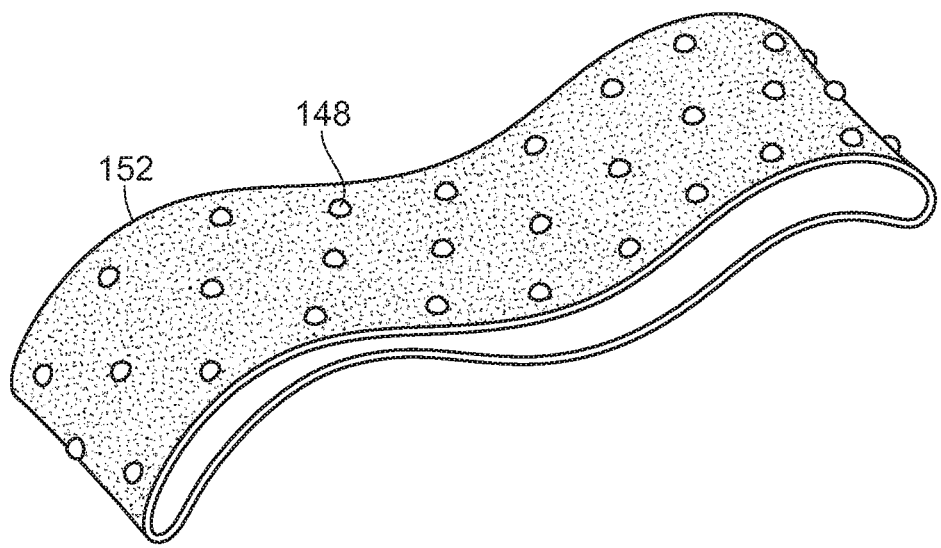
FIG. 7 is a perspective view of an embodiments of a flexible cleaning band in accordance with the present disclosure.

Referring to FIG. 7, a perspective view of an embodiment of the first cleaning band 152 is shown. Please note that in many embodiments, the first cleaning band 152 and the second cleaning band 162 (See FIG. 5) are identical in construction with the exception of their sizes. Here, the embodiments of the first cleaning band 152 is equipped with an abrasive material to aid in the cleaning of the user's foot and to assist with the removal of any calluses. Such abrasive materials include sand, coral, quartz, glass, zirconia, cubic zirconia, turquoise, amethyst, black obsidian, emeralds, diamonds, and rubies.

In a preferred embodiment, the fluid inserted in the tank in accordance with the present disclosure is water. In other embodiments, the fluid is water infused with essence oils. In a highly preferred embodiment, the automatic foot cleaner and callus remover 100 is equipped with a device that will dispense a pre-determined amount of essence oil into the tank. Preferably, this amount will be configurable by the user by entering their preference into the associated computer.

In various embodiments, the automatic foot cleaner and callus remover 100 is equipped with a computer having a processor and a memory containing computer-readable instructions as to how to operate the automatic foot cleaner and callus remover 100, where the processor and memory are in electronic communication with a power supply and the first motor 156, the second motor 166, the third motor 172, and/or the fourth motor 168. Preferably, the computer will provide a user with a number of pre-determined cleaning settings, allowing the user to directly create their entire preference on the automatic foot cleaner and callus remover 100 through the use of one or more integrated buttons, or the user can select their preference through the use of a smartphone application which interfaces with the computer through the Internet. Alternatively, a user will be able to select the type of actuation and the length of actuation for the sole cleaning mechanism 160, the toe cleaning mechanism 170, and the heel cleaning mechanism 150. Preferably, after the automatic foot cleaner and callus remover 100 has operated for the selected amount of time, it will automatically shut off.

In a preferred embodiment, the automatic foot cleaner and callus remover 100 is also equipped with a drain having a drain hole and a removably attached drain stopper, where the drain is integrated into the tank 120 and the drain reservoir 128. When the removably attached drain stopper is removed, any fluid in the tank will be expelled by gravity.

In yet another embodiment, the toe cleaning mechanism 170 can have a different configuration. Instead of a single cleaning member that is parallel with the heel cleaning mechanism 150, the toe cleaning mechanism 170 can be constructed out of four rotating brushes that are parallel with the sole cleaning mechanism 160. Each of these four rotating brushes will correspond to one of the gaps between the toes of a human user, and will be in electronic communication with the computer and the power source. Each of these brushes can be actuated in the same direction, or can be independently actuated as desired by the user.

It is understood that when an element is referred hereinabove as being "on" another element, it can be directly on the other element or intervening elements may be present therebetween. In contrast, when an element is referred to as being "directly on" another element, there are no intervening elements present.

Moreover, any components or materials can be formed from a same, structurally continuous piece or separately fabricated and connected.

It is further understood that, although ordinal terms, such as, "first," "second," and "third," are used herein to describe various elements, components, regions, layers and/or sections, these elements, components, regions, layers and/or sections should not be limited by these terms. These terms are only used to distinguish one element, component, region, layer and/or section from another element, component, region, layer and/or section. Thus, a "first element," "component," "region," "layer" and/or "section" discussed below could be termed a second element, component, region, layer and/or section without departing from the teachings herein.

Features illustrated or described as part of one embodiment can be used with another embodiment and such variations come within the scope of the appended claims and their equivalents.

Spatially relative terms, such as "beneath," "below," "lower," "above," "upper" and the like, are used herein for ease of description to describe one element or feature's relationship to another element(s) or feature(s) as illustrated in the figures. It is understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device can be otherwise oriented (rotated 90 degrees or at other orientations) and the spatially relative descriptors used herein interpreted accordingly.

Example embodiments are described herein with reference to cross section illustrations that are schematic illustrations of idealized embodiments. As such, variations from the shapes of the illustrations, for example, of manufacturing techniques and/or tolerances, are to be expected. Thus, example embodiments described herein should not be construed as limited to the particular shapes of regions as illustrated herein, but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

As the invention has been described in connection with what is presently considered to be the most practical and various embodiments, it is to be understood that the invention is not to be limited to the disclosed embodiments, but on the contrary, is intended to cover various modifications and equivalent arrangements included within the scope of the appended claims. Although specific terms are employed herein, they are used in a generic and descriptive sense only and not for purposes of limitation.

This written description uses examples to disclose the invention, including the best mode, and also to enable any person skilled in the art to practice the invention, including making and using any devices or systems and performing any incorporated methods. The patentable scope of the invention is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

In conclusion, herein is presented an automatic foot cleaner and callus remover. The disclosure is illustrated by example in the drawing figures, and throughout the written description. It should be understood that numerous variations are possible while adhering to the inventive concept. Such variations are contemplated as being a part of the present disclosure.

What is claimed is:

1. An automatic foot cleaner and callus remover, comprising:
    a housing having a front end, a rear end, a left side and a right side both extending between the front end and the rear end, a bottom extending between the front end, the rear end, the left side and the right side, a top extending between the front end, the rear end, the left side and the right side, and an outer shell bounded by the front end, the rear end, the left side, the right side, the bottom, and the top,
        wherein the top is shaped and sized to accommodate the insertion of a human foot into the housing;
    a plurality of interior walls contained within the housing,
        wherein the plurality of interior walls form a fluid-impermeable tank, the tank having a drain reservoir and a drain having an open position and a closed position, the drain comprising a drain hole and a removably attached drain stopper,
        wherein the tank is shaped such that a fluid disposed in the tank will flow into the drain reservoir,
        wherein the drain is located such that gravity will direct fluids outside of the housing when the drain is in the open position;
    a cavity, defined by the plurality of interior walls and the outer shell;
    a heel cleaning mechanism proximate to the rear end, comprising a heel resting member disposed on the bottom, within the tank, a first motor located within the cavity, a first plurality of rollers a first portion of which is located within the cavity, a second portion of which is located within the tank, and a first cleaning band,
        wherein the first cleaning band provides for the mechanical communication between the first motor and the first plurality of rollers,
        wherein the first cleaning band is flexible,
        wherein the first cleaning band is equipped with at least one abrasive material,
        wherein the first motor is configured to actuate the first cleaning band,
    a sole cleaning mechanism, comprising a second motor located within the cavity,
    a second plurality of rollers located within the tank, and a second cleaning band,
        wherein the second cleaning band provides for the mechanical communication between the second motor and the second plurality of rollers,
        wherein the second cleaning band is flexible,
        wherein the second cleaning band is equipped with the at least one abrasive material,
        wherein the second motor is configured to actuate the second cleaning band,
        wherein the second cleaning band extends from the left side to the right side,
    a toe cleaning mechanism proximate to the front end, comprising a third motor located within the cavity, a cleaning member that extends from the third motor into the tank,
        wherein the cleaning member is equipped with a plurality of bristles,
        wherein the third motor is configured to rotatably actuate the cleaning member;
    a power source in electronic communication with the first motor, the second motor, and the third motor; and
    a processor and a memory, both in electronic communication with each other and the power source, the memory containing computer-readable instructions for the selective actuation of the first motor, the second motor, and the third motor.

2. The automatic foot cleaner and callus remover of claim 1, further comprising a guidance insert which is shaped to rest on the top,
    wherein the guidance insert is sized and shaped to accommodate the insertion of a human foot into the housing.

3. The automatic foot cleaner and callus remover of claim 2, further comprising an essence oil infuser, configured to dispense one or more essence oils into the tank.

4. The automatic foot cleaner and callus remover of claim 3, the at least one abrasive material being selected from the group consisting of: sand, coral, quartz, glass, zirconia, cubic zirconia, turquoise, amethyst, black obsidian, emeralds, diamonds, and rubies.

5. The automatic foot cleaner and callus remover of claim 4, wherein the first motor is configured to continuously actuate the first cleaning band.

6. The automatic foot cleaner and callus remover of claim 4, wherein the first motor is configured to alternatingly actuate the first cleaning band.

7. The automatic foot cleaner and callus remover of claim 4, wherein the second motor is configured to continuously actuate the second cleaning band.

8. The automatic foot cleaner and callus remover of claim 4, wherein the second motor is configured to alternatingly actuate the second cleaning band.

9. The automatic foot cleaner and callus remover of claim 4, further comprising a fourth motor located within the cavity
    wherein the fourth motor is in mechanical communication with the second motor, the second plurality of rollers, and the second cleaning band, wherein the fourth motor is in electronic communication with the power source, the processor, the memory, and the second motor.

* * * * *